US008736263B2

(12) United States Patent
Minh (10) Patent No.: US 8,736,263 B2
(45) Date of Patent: May 27, 2014

(54) SYSTEM AND METHOD FOR ESTIMATING FORMATION CHARACTERISTICS IN A WELL

(75) Inventor: Chanh Cao Minh, La Defense (AO)

(73) Assignee: Schlumberger Technology Corporation, Sugar Land, TX (US)

(*) Notice: Subject to any disclaimer, the term of this patent is extended or adjusted under 35 U.S.C. 154(b) by 1158 days.

(21) Appl. No.: 12/669,590

(22) PCT Filed: Jul. 24, 2008

(86) PCT No.: PCT/US2008/070959
§ 371 (c)(1),
(2), (4) Date: Jun. 23, 2010

(87) PCT Pub. No.: WO2009/015252
PCT Pub. Date: Jan. 29, 2009

(65) Prior Publication Data
US 2010/0264914 A1    Oct. 21, 2010

Related U.S. Application Data

(60) Provisional application No. 60/952,003, filed on Jul. 26, 2007.

(51) Int. Cl.
    *G01V 3/00* (2006.01)
(52) U.S. Cl.
    USPC .......................................... 324/303
(58) Field of Classification Search
    USPC ................................. 324/300–322
    See application file for complete search history.

(56) References Cited

U.S. PATENT DOCUMENTS

| 5,828,214 A | 10/1998 | Taicher et al. |
| 6,088,656 A * | 7/2000 | Ramakrishnan et al. ....... 702/13 |
| 6,229,308 B1 | 5/2001 | Freedman |
| 6,541,969 B2 * | 4/2003 | Sigal et al. .................... 324/303 |
| 6,856,132 B2 * | 2/2005 | Appel et al. .................. 324/303 |
| 6,903,547 B2 * | 6/2005 | Sigal et al. .................... 324/303 |
| 6,954,066 B2 * | 10/2005 | Siess et al. .................... 324/303 |
| 7,176,682 B2 * | 2/2007 | Galford et al. ................ 324/303 |
| 7,224,162 B2 * | 5/2007 | Proett et al. ................... 324/303 |
| 7,463,027 B2 * | 12/2008 | Prammer et al. .............. 324/303 |
| 7,538,547 B2 * | 5/2009 | Heaton ......................... 324/303 |
| 7,652,950 B2 * | 1/2010 | Sinha et al. .................... 367/31 |
| 7,733,086 B2 * | 6/2010 | Prammer et al. .............. 324/303 |

(Continued)

OTHER PUBLICATIONS

N. Heaton et al., "4D NMR—Applications of the Radial Dimension in Magnetic Resonance Logging," SPWLA 48th Annual Logging Symposium,, pp. 1-15, Austin, Texas (Jun. 3-6, 2007).

(Continued)

*Primary Examiner* — Dixomara Vargas
(74) *Attorney, Agent, or Firm* — Kenneth Liu; Jeremy Berman (57) ABSTRACT

A technique utilizes the acquisition of data via nuclear magnetic resonance at multiple depths of investigation in a well region. The acquired data is processed to estimate variable fluid mixture densities at different radial depths. The variable fluid mixture densities and a radial response from a density tool, for example, can be used to calculate an effective fluid mixture density and used to interpret density logs. Other logs such as neutron log, induction resistivity log, and dielectric permittivity log can be combined with NMR. For these tools a corresponding effective formation property can be calculated and used to determine other formation characteristics, such as total porosity, total density, dielectric permittivity, electric resistivity, and formation characteristics derivable from these.

23 Claims, 13 Drawing Sheets

(56) References Cited

U.S. PATENT DOCUMENTS

| | | | |
|---|---|---|---|
| 7,741,841 B2 * | 6/2010 | Edwards et al. | 324/303 |
| 8,374,974 B2 * | 2/2013 | Chen et al. | 706/8 |
| 8,452,538 B2 * | 5/2013 | Klein et al. | 702/7 |
| 2003/0006767 A1 | 1/2003 | Georgi et al. | |
| 2004/0027122 A1 | 2/2004 | Heaton et al. | |
| 2004/0222791 A1 | 11/2004 | Chen | |

OTHER PUBLICATIONS

Gaymard, R. et al., "Response of neutron and Formation Density Logs in Hydrocarbon Bearing Formations," The Log Analyst at vol. IX, No. 5 (Sep.-Oct. 1968) 18 pages.

Suau, J., "An Improved Gas Correction Method for Density and Neutron Logs," Annual SPWLA Logging Symposium (Jun. 1981) 19 pages.

Freedman, R. et al., "Combining NMR and Density Logs for Petrophysical Analysis Gas-Bearing Formations," SPWLA Annual Logging Symposium, (May 1998) 14 pages.

Casu, P.A. et al., "Using Consonant-Measurement Sensors for a More Accurate Log Interpretation," SPWLA Annual Logging Symposium (May 1998) 14 pages.

Minh et al., "Planning and Interpreting NMR Fluid-Characterization Logs," SPE 84478, Annual Technical Conference and Exhibit, (Oct. 2003) 12 pages.

Heaton, N. et al., "4D NMR—Applications of the Radial Dimension in Magnetic Resonance Logging," SPWLA Annual Logging Symposium (Jun. 2007) 15 pages.

Sherman, H. et al., "Depth of Investigation of Neutron and Density Sondes for 35-Percent-Porosity Sand," SPWLA Annual Logging Symposium (Jun. 1975) 14 pages.

* cited by examiner

SYSTEM AND METHOD FOR ESTIMATING FORMATION CHARACTERISTICS IN A WELL

CROSS-REFERENCE TO RELATED APPLICATION

The present document is based on and claims priority to U.S. Provisional Application Ser. No. 60/952,003, filed Jul. 26, 2007.

BACKGROUND

In various well related operations, the density of the rock matrix and the fluid are needed for proper interpretation of the log measurements and other decisions. The matrix density of a formation can be determined from core analysis or spectroscopy logging. However, these techniques do not enable estimation of the apparent fluid density. In many applications, near-wellbore fluids composition and distribution can be very complex. For example, wells drilled with oil-based mud can create near-wellbore fluid compositions with a variety of fluids in complex distributions. Currently, density/total porosity is computed by using an ad hoc constant fluid density. However, the fluid density often is complex rather than constant and thus use of constant fluid density can lead to erroneous estimations of porosity.

Studies have been conducted regarding near-wellbore fluids to investigate near-wellbore fluid mixtures at a single depth of investigation. For example, three dimensional nuclear magnetic resonance (T1, T2, D) maps have been created regarding fluid measurements at the single depth of investigation. In some environments, very complex fluid mixtures can include a variety of fluids, including water, oil, oil-base mud, and condensate/gas. However, fluid maps acquired at a single depth of investigation cannot be relied on as representative of the fluids mixture measured by the density logging tool.

SUMMARY

The present invention provides a system and method for acquiring data via nuclear magnetic resonance at multiple depths of investigation. The acquired data is processed to estimate variable fluid mixture densities at different radial depths corresponding to the depths of investigation of the NMR tool. The variable fluid mixture densities and a radial response from a density tool can be used to calculate an effective fluid mixture density. This is the fluid mixture density as seen by the density tool and can be used to interpret density logs. Other logs such as neutron log, induction resistivity log, and dielectric permittivity log can be combined with NMR. For these tools a corresponding effective formation property can be calculated and used to determine other formation characteristics, such as total porosity, total density, dielectric permittivity, electric resistivity, and formation characteristics derivable from these.

BRIEF DESCRIPTION OF THE DRAWINGS

Certain embodiments of the invention will hereafter be described with reference to the accompanying drawings, wherein like reference numerals denote like elements, and.

DETAILED DESCRIPTION

In the following description, numerous details are set forth to provide an understanding of the present invention. However, it will be understood by those of ordinary skill in the art that the present invention may be practiced without these details and that numerous variations or modifications from the described embodiments may be possible.

The present invention generally relates to a system and method for improving the accuracy of estimates related to well parameters. For example, the system and methodology enable accurate estimations of variable fluid mixture densities at multiple radial positions into the formation as characterized by depths of investigation (DOI) of a measuring tool along a given well region. The accurate understanding of variable fluid mixture densities can be used in determining other parameters related to the well, such as total porosity.

Nuclear magnetic resonance (NMR) tools can be used in a well region to obtain the desired data for determining variable fluid mixture densities. For example, three dimensional nuclear magnetic resonance techniques can be used to obtain data from the near-wellbore regions surrounding a given wellbore. Furthermore, the advent of radial fluid profiling with magnetic resonance tools can provide a fourth dimension in the form of radial information which can be inverted jointly with conventional three-dimensional nuclear magnetic resonance data to unravel both fluids mixture and radial distribution of the fluids. Because the near-wellbore NMR region closely matches the density region in both radial and axial directions, the two sets of data form "perfect" consonant volumes. Continuous four dimensional NMR maps are thus able to provide ideal estimates of the variable mixed fluids density. The value can be expressed as the double integration of all individual fluids detected by NMR weighted by the geometrical radial response function of the density log. In this example, the inner integration provides an estimate of the mixed fluids density, and the outer integration computes it at approximately 95% radial response of the density log.

Accordingly, the present system and methodology enable accurate estimation of variable fluid mixture density with multidimensional NMR at multiple depths of investigation. The variable fluid mixture density data can then be used to determine other well related characteristics, such as computing a density porosity assuming matrix density is known. As a result, formation characteristics, such as density porosity, can be determined much more accurately than through use of conventional techniques, such as the use of an ad hoc constant fluid density over large intervals. The methodology provides an effective technique for accurately determining a formation property such as variable fluid mixture densities in this case and using the variable fluid mixture densities to estimate, for example, total porosity from a density log free of a hydrocarbon effect. The methodology also provides the additional benefit of reconciling the NMR and density porosities.

In the description below, examples are provided in which the data acquired on variable fluid densities confirms subtle fluid changes recorded by density-neutron logs in a variety of formations, such as sandstone formations. In the sandstone formation example, the sands have variations in grain size and shaliness that control permeability and therefore the oil-base mud (OBM) filtrate invasion. In another example, the data is used to determine large porosity deficits when the contrasting fluids density is large, such as when a gas is invaded by oil-base mud.

Figure 1:
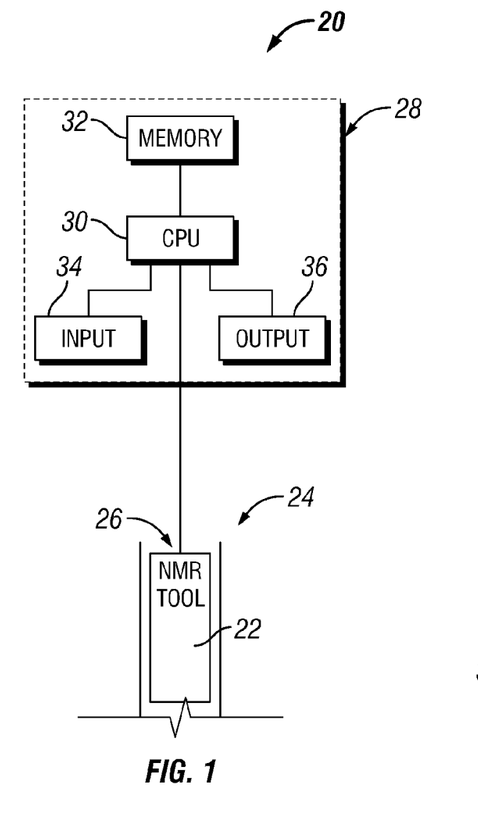
FIG. 1 is a schematic illustration of a system for estimating variable fluid mixture densities along a well region, according to an embodiment of the present invention.

Referring generally to FIG. 1, a well system 20 is illustrated according to one embodiment of the present invention. Well system 20 is designed to facilitate estimation of one or more well related characteristics. In the environment illustrated, well system 20 comprises a nuclear magnetic resonance (NMR) tool 22, such as an NMR logging tool, for acquiring data from a well 24. The acquired data is related to variable fluid mixture densities and is acquired at multiple depths of investigation. For example, the NMR tool 22 can be moved along a wellbore 26 while collecting data at multiple depths of investigation throughout an entire region of well 24.

The illustrated well system 20 further comprises a processor based system 28 in communication with NMR tool 22 to receive acquired data. Some or all of the methodology outlined below may be carried out by the processor based system 28. By way of example, processor based system 28 is an automated system that may be a computer-based system having a central processing unit (CPU) 30. CPU 30 may be operatively coupled to NMR tool 22. In the illustrated example, system 28 further comprises a memory 32 as well as an input device 34 and an output device 36. Input device 34 may comprise a variety of devices, such as a keyboard, mouse, voice-recognition unit, touchscreen, other input devices, or combinations of such devices. Output device 36 may comprise a visual and/or audio output device, such as a monitor having a graphical user interface. Additionally, the processing may be done on a single device or multiple devices downhole, at the well location, away from the well location, or with some devices located at the well and other devices located remotely. The NMR tool 22 may be conveyed downhole by wireline, coil tubing, as part of a drill string (LWD tool), or any mode of conveyance used in oil industry. The processor 28 can be located inside the tool and perform the analysis downhole, pr partially downhole, or it may be located uphole where it receives data from downhole tool via a wireline, or a telemetry commonly used for LWD tools. One such telemetry will be wired drill pipe.

Figure 2:
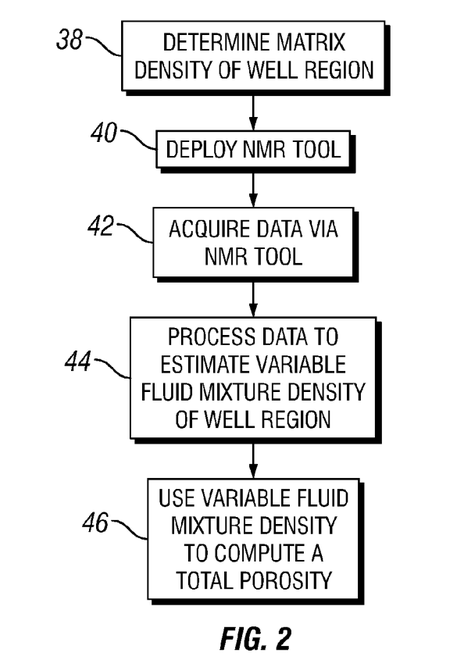
FIG. 2 is a flowchart illustrating one process for estimating fluid characteristics along a well region, according to an embodiment of the present invention.

The processor based system 28 can be utilized in the analysis of data acquired by the NMR tool 22 to provide accurate estimates of subject well characteristics. One example of a general application is illustrated by the flowchart of FIG. 2. In this example, the matrix density of a well region is initially determined, as illustrated by block 38. Subsequently, the NMR tool 22 is deployed in the well region, as illustrated by block 40. The NMR tool may comprise an NMR logging tool which is selectively moved along wellbore 26 to acquire data, as illustrated by block 42. In some applications, data can be acquired by a single pass of the logging tool through wellbore 26. Once acquired, the data is processed to estimate variable fluid mixture densities along the well region, as illustrated by block 44. The variable fluid mixture densities can be used in computing a selected well characteristic or characteristics, such as total porosity, as illustrated by block 46.

Figure 3:
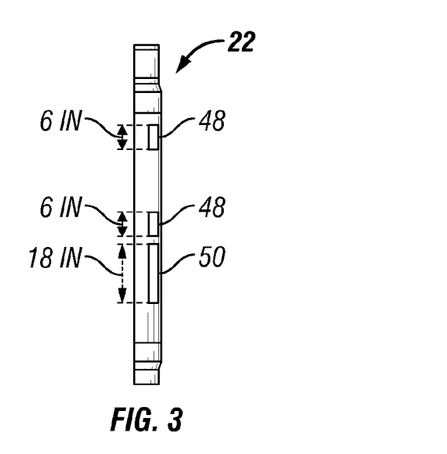
FIG. 3 is one example of a magnetic resonance tool used to acquire data along a well region, according to an embodiment of the present invention.
Figure 4:
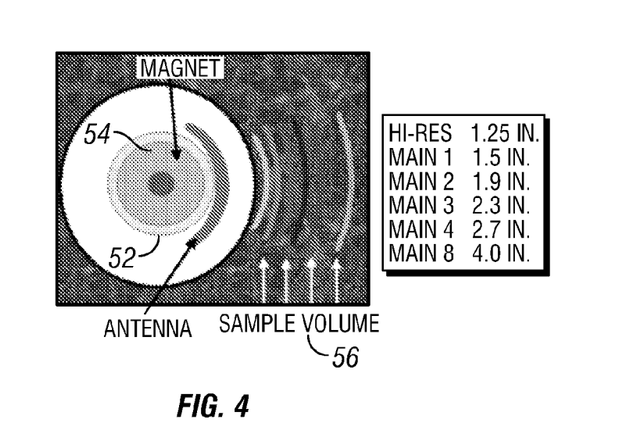
FIG. 4 is a top view of the magnetic resonance tool deployed in a wellbore, according to an embodiment of the present invention.

By way of example, the NMR tool 22 may comprise an NMR logging tool, as illustrated in FIG. 3. The illustrated NMR logging tool 22 comprises a plurality of antennas, such as high-resolution antennas 48 and a main antenna 50. The NMR logging tool 22 also may comprise an outer housing 52 enclosing a magnet 54, as best illustrated in FIG. 4. In this embodiment, the NMR logging tool 22 is designed to implement four dimensional NMR logging which adds a radial dimension. The logging tool is able to provide data for the creation of continuous fluid maps at multiple depths of investigation, sometimes referred to as shells 56. By way of example, the shells may be at specific radial depths, such as 1 inch, 2.7 inches, 4 inches or other radial distances. The simultaneous processing of data from all shells is designed to optimize the fluid results. One example of a suitable NMR logging tool 22 is the MR Scanner™ tool available from Schlumberger Corporation of Houston, Tex.

Figure 5:
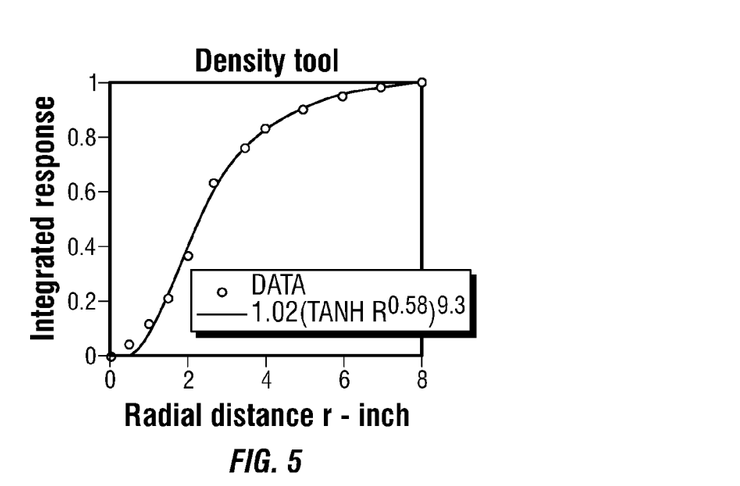
FIG. 5 is graphical representation showing a radial response of a density tool approximated by a hyperbolic tangent function of a radial distance, according to an embodiment of the present invention.
Figure 6A:
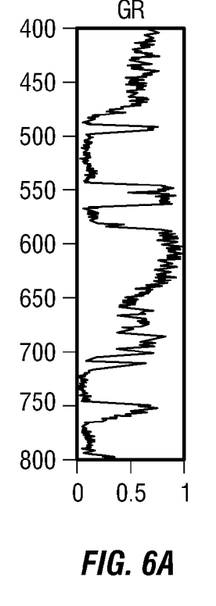
FIG. 6 is a graphical representation showing open hole logs manifesting large gas effects, according to an embodiment of the present invention.
Figure 6B:
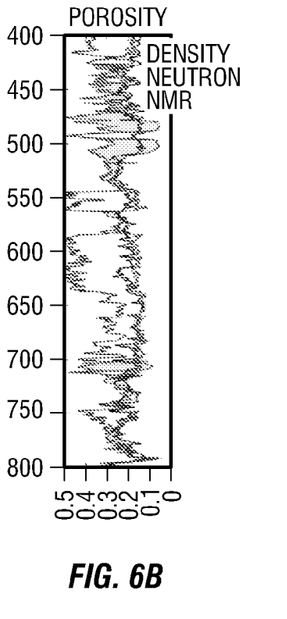
Figure 6C:
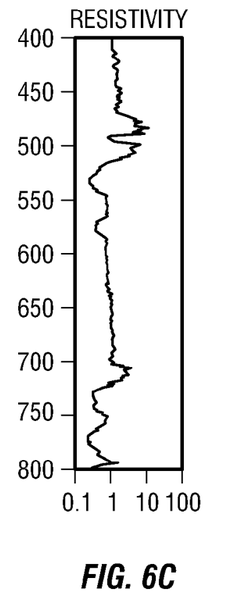
Figure 6D:
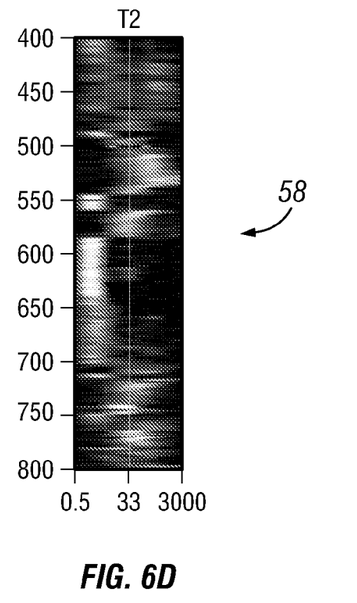
Figure 7A:
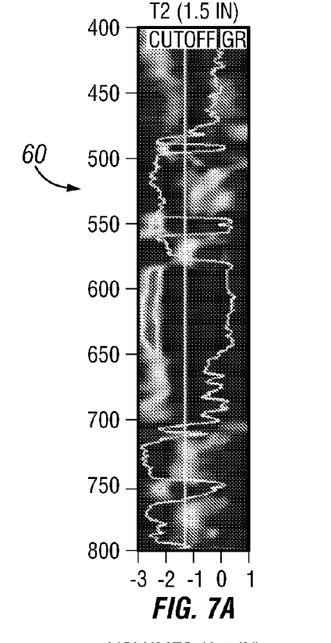
FIG. 7 is a graphical representation showing radial fluid analysis through application of four dimensional nuclear magnetic resonance logging, according to an embodiment of the present invention.
Figure 7B:
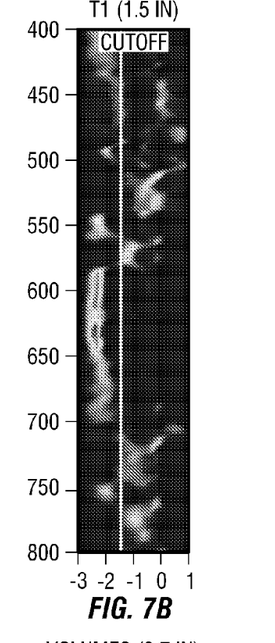
Figure 7C:
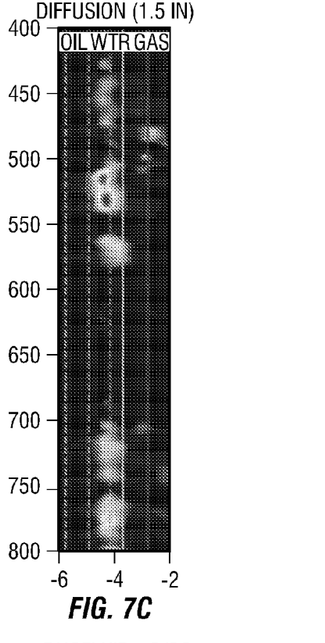
Figure 7D:
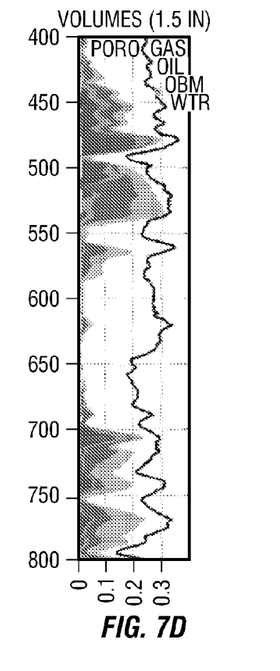
Figure 7E:
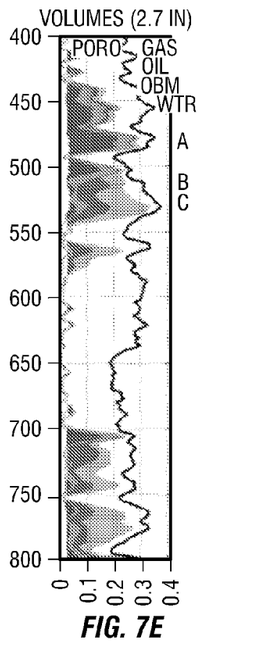
Figure 7F:
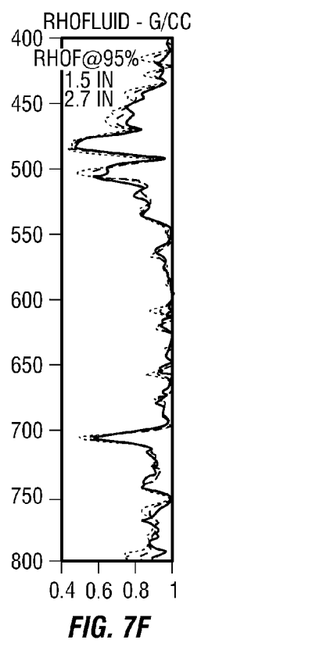
Figure 8A:
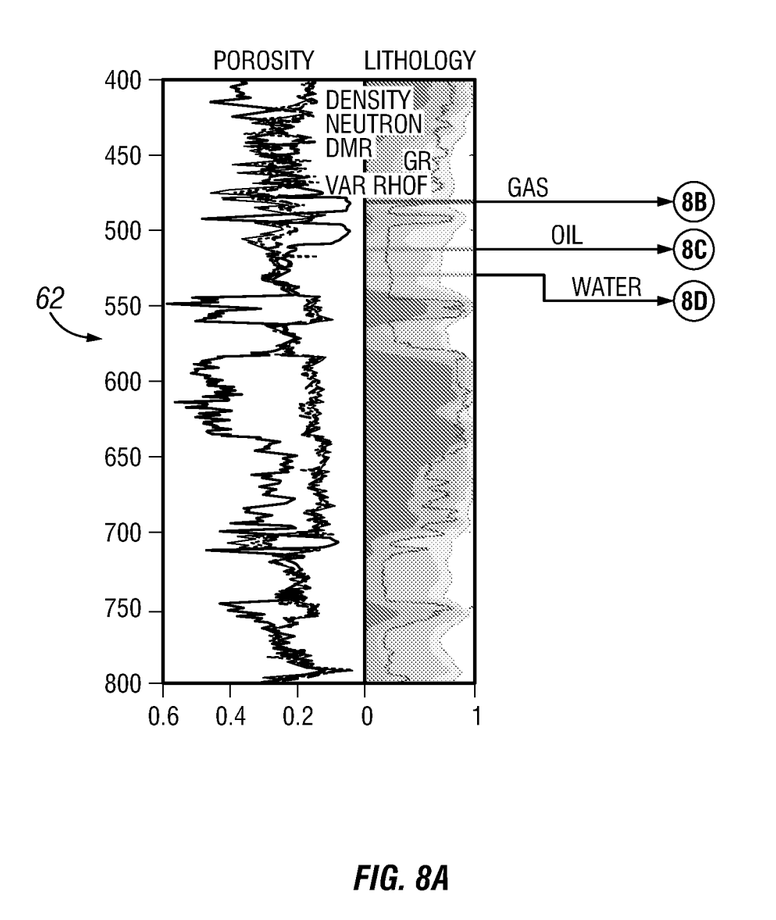
FIG. 8 is a graphical representation showing a porosity comparison between DMR and variable fluid density techniques in which radial fluid distribution D-T1 maps are shown for a gas zone, an oil zone, and a water zone, according to an embodiment of the present invention.
Figure 8B:
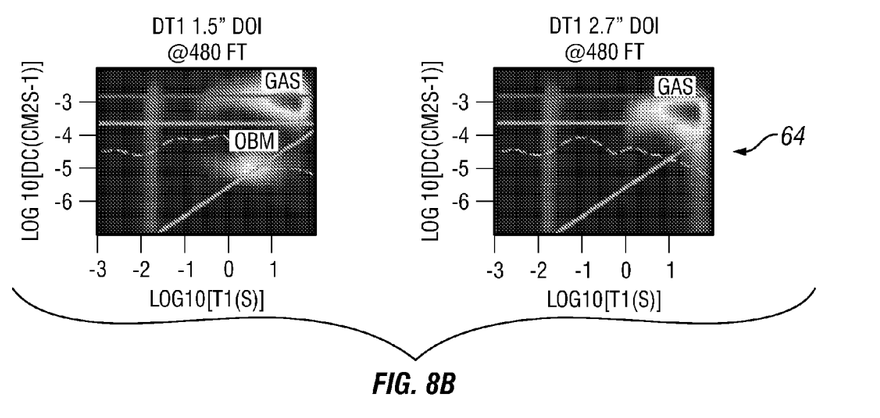
Figure 8C:
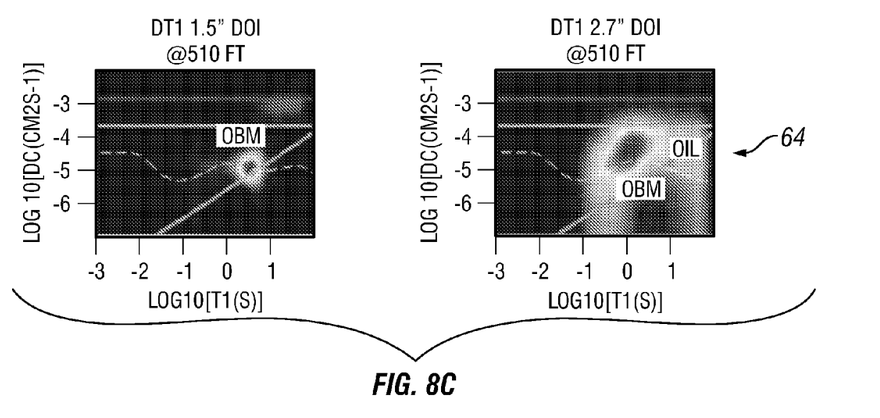
Figure 8D:
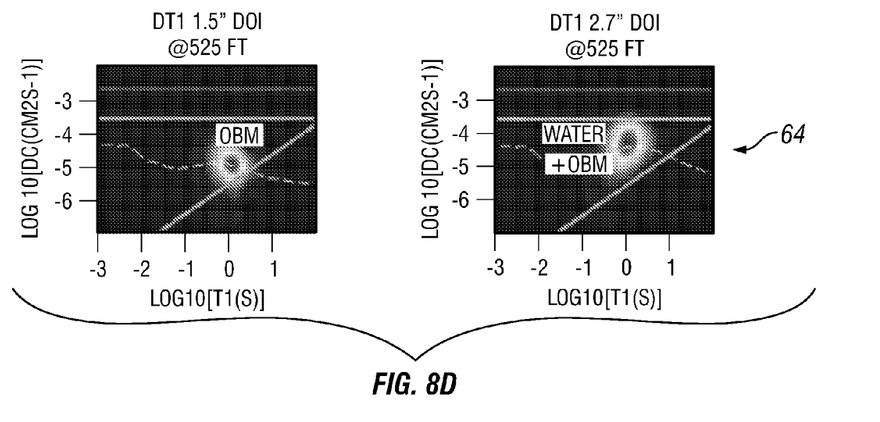

A technique for estimating formation characteristics in a well is described in greater detail below along with examples and illustrations. According to one embodiment, the technique is accomplished by collecting the desired data via NMR tool 22, transferring the data to processor based system 28, and processing the data using a suitable method, such as 4-D NMR, to derive the fluid saturations at radial depths corresponding to the NMR tool's depths of investigation. The fluid saturations can be converted to the fluid density at these radial depths by multiplying with individual fluid densities. The system 28 can also calculate an effective fluid density which is the density integrated over the volume of investigation of the density tool according to the formulas and approach described herein. To better understand the descriptions and examples provided below, the following nomenclature is used:

T2 transverse relaxation time
T1 longitudinal relaxation time
D Diffusion constant
$\rho_{fluid}$ Effective fluid mixture density up to 95% response of density tool
$S_i$ i-th fluid saturation $\rho_i$ i-th fluid density
nf number of fluids
J Density geometrical radial response
r radial distance from wellbore The effective fluid mixture density ($\rho_{fluid}$) can be expressed as the double integration of all individual fluids density weighted by the geometrical radial response function of the density log:

$$\rho_{fluid} = \int J(r)dr \int_{i=1}^{i=nf} S_i(r)\rho_i \, di \qquad (1)$$

where $S_i$ and $\rho_i$ are the i-th fluid saturation and density respectively, nf is the number of fluids, usually 4 (water, oil, gas, OBM filtrate) but can be more, the function J(r) is the differentiated geometrical radial response of the density tool as defined by Sherman and Locke (1975). (Sherman H. and Locke S., 1975, "Depth of Investigation of Neutron and Density Sondes for 35-percent Porosity Sand", Annual SPWLA Logging Symposium Transactions, paper Q, New Orleans, La., USA.) Their published data can be approximated by a hyperbolic tangent function of the radial distance, r, as illustrated by the graph in FIG. 5.

The general expression of J(r) is thus:

$$J(a,r) = a(1)(\tan h(r^{a(2)}))^{a(3)}. \qquad (2)$$

Because the inner integration yields the fluid mixture density at a given value of r, the solution to equation (1) becomes a non-linear extrapolation problem, i.e. from NMR-derived fluid densities at various DOIs, find the fluid density from r=0 to 6 in. (which corresponds to 95% of the radial response of the density tools).

When using the NMR tool 22, e.g. the MR Scanner™ tool, the available data points occur at specific depths in the formation from borehole wall, e.g. at 1.5 in., 2.7 in, and 4 in. inside the formation. Thus, in this example the dimension of the input data vector for the extrapolation is 4 (when the origin point at the borehole wall is also included). The coefficient vector, a, minimizes the norm as follows:

$$\min_a \frac{1}{2} \sum_{j=1}^{4} (J(a, r_j) - \rho_j)^2 \qquad (3)$$

where $\rho_j$ is the j-th NMR fluid mixture density at a radial distance, $r_j$ and $J(a,r_j)$ is the vector-value function to be fit. The equation is first solved at every depth level, then the effective fluid mixture density is estimated via equation (2) at r=6 in.

A good approximation to the solution of equation (1) is set forth below. It should be noted with respect to FIG. 3, the density geometrical factors at 1.5 in., 2.7 in. and 4 in. are 0.21, 0.63 and 0.83 respectively. Thus, the effective fluid mixture density $\rho_{fluid}$ at the deepest DOI, r=4 in., might be estimated as:

$$\rho_{fluid} = (0.21\rho_{1.5} + 0.42\rho_{2.7} + 0.2\rho_4)/0.83 \qquad (4)$$

where 0.21, 0.42, and 0.2 are the differences between adjacent J(r) values and $\rho_{1.5}$, $\rho_{2.7}$, and $\rho_4$ are the fluid mixture densities at 1.5 in., 2.7 in. and 4 in. radial depths respectively. Equation (4) shows the fluid density at 2.7 in. has the largest coefficient and contributes the most to the fluid mixture density. However, this is only true for estimating the density up to 4 inch from the borehole and may not be true for $\rho_{fluid}$ at 6 in. radial depth.

Example 1

Gas-Bearing Reservoirs

A first example is provided for a gas-bearing sandstone reservoir drilled with OBM. In this example, the sands are often unconsolidated with excellent porosity and permeability. The sands matrix density is 2.65 g/cc, which can be determined from core data in nearby wells.

Referring to FIG. 6, openhole logs 58 are illustrated and include a high-resolution 1D NMR T2 log in track 4. The hydrocarbon intervals are at shaded depths where the density and neutron logs illustrated in track 2 do not overlap. In this example, at around 500 ft and 700 ft, the gas effect ranges from 40 pu to 30 pu, making accurate determination of true porosity difficult.

Traditionally, a constant fluid density would have been used to compute porosity from the density log that gives the best match with core porosity. However, in this example no core data is taken from the well. As a result, the selection of the fluid density in the water zone, oil zone, gas zone and shale zones is left to the skill of the interpreter. At the wellsite, a constant fluid density of 0.9 g/cc is used as a compromise for various fluids mixture. The best-known fluids parameters are summarized below:

|  | Gas | Oil | OBM | Water |
| --- | --- | --- | --- | --- |
| Density (g/cc) | 0.2 | 0.75 | 0.85 | 1.0 |
| Hydrogen Index | 0.4 | 1 | 1 | 1 |
| T1 @BHT (s) | 4 | >2 | ~1 | <1 |

In this example, the well also can be logged with a saturation-profiling mode (3D NMR) via NMR tool 22 for fluid evaluation at 1.5 in DOI and 2.7 in DOI. The fluid data acquired can then be processed via processor based system 28 according to a four dimensional (4D) NMR technique. The processed data results can be displayed on, for example, as illustrated in FIG. 7.

In FIG. 7, a plurality of tracks 60 is illustrated. The first 3 tracks display T2, T1 and D respectively for the 1.5 in DOI dataset, the data for 2.7 inch is not shown. The fluid volumes for both DOIs are displayed in track 4 and track 5 respectively. Track 6 shows the variable fluid densities at both DOIs and the estimated fluid density at 95% response (labeled as rhof). It can be seen that the fluid density varies from a low value of 0.45 g/cc in gas sands to a high value of 1 g/cc in shales.

FIG. 7 further illustrates changes in fluid density. For example, point A in a gas zone at 480 ft, point B in an oil zone at 510 ft, and point C in a water zone at 525 ft are selected to illustrate how the fluid density can change continuously.

Figure 9:
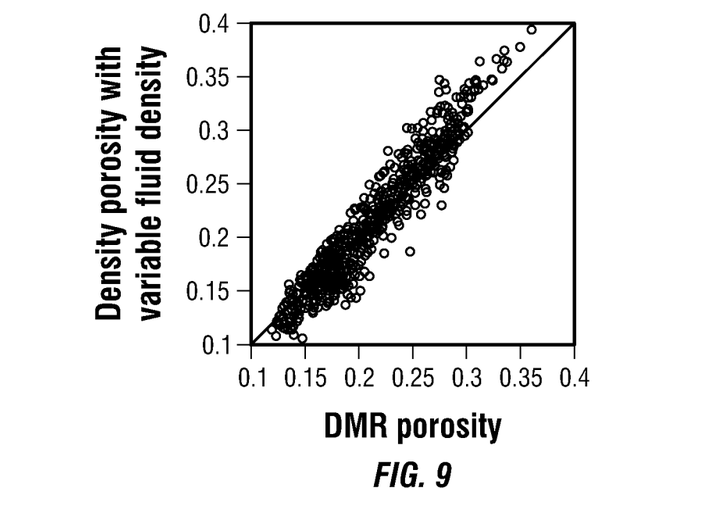
FIG. 9 is a graph comparing DMR porosity along the x-axis and fluid density porosity from the method of this invention along the y-axis.
Figure 10A:
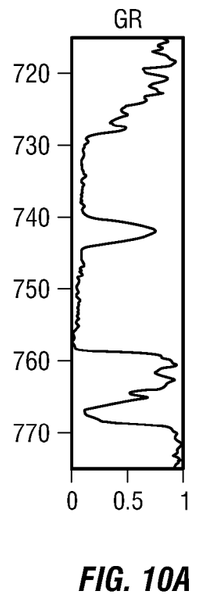
FIG. 10 is a graphical representation illustrating open hole logs, according to an embodiment of the present invention.
Figure 10B:
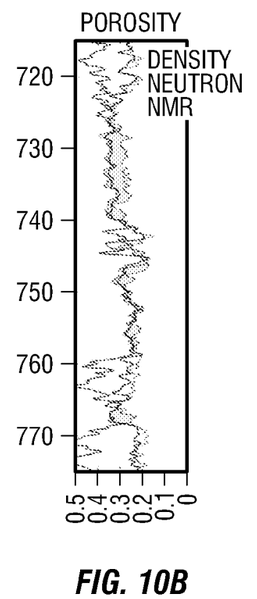
Figure 10C:
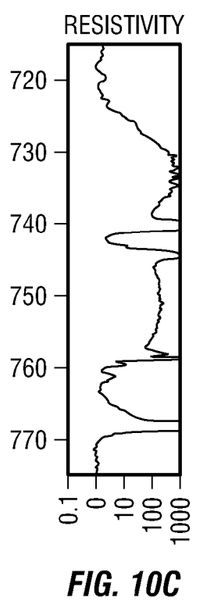
Figure 10D:
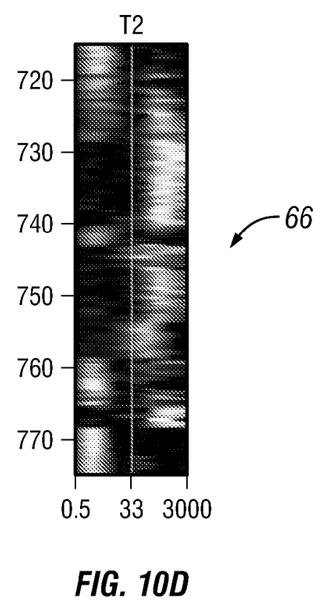
Figure 11A:
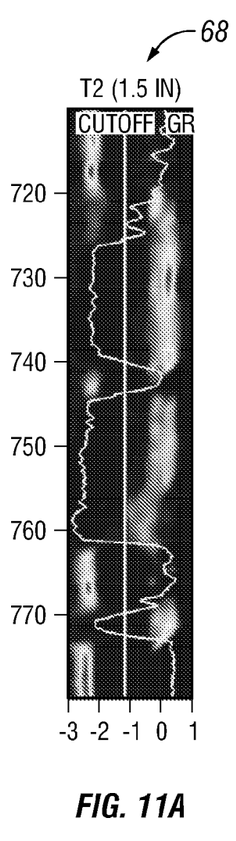
FIG. 11 is a graphical representation illustrating radial fluid analysis utilizing four dimensional nuclear magnetic resonance logging to show decreasing oil-base mud invasion with increasing depth of investigation, according to an embodiment of the present invention.
Figure 11B:
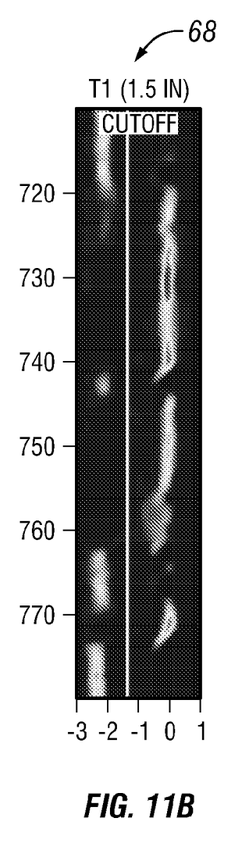
Figure 11C:
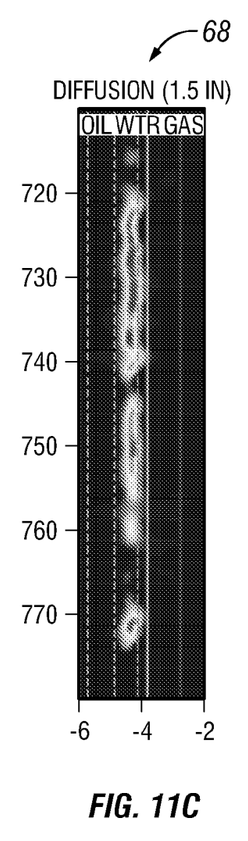
Figure 11D:
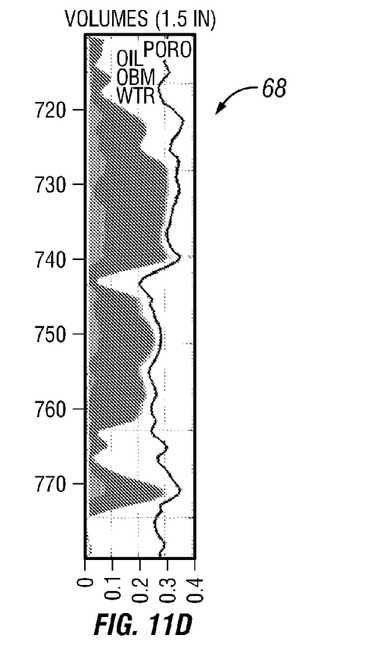
Figure 11E:
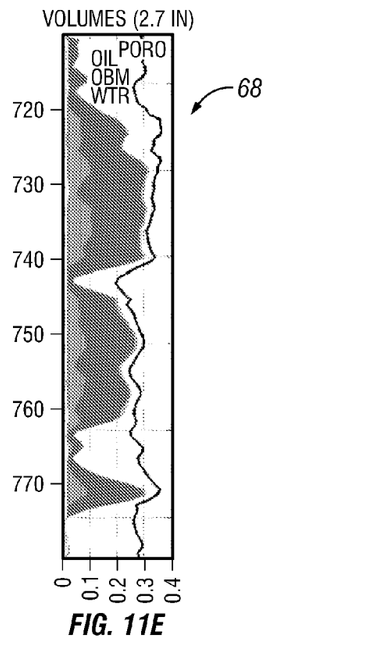
Figure 11F:
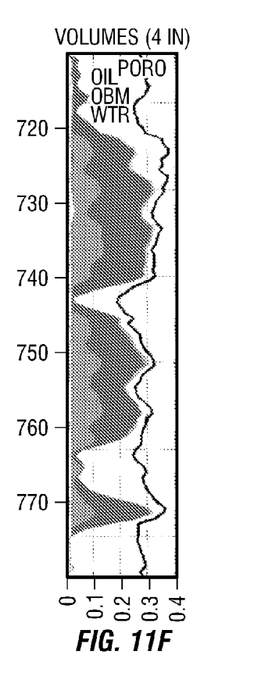
Figure 11G:
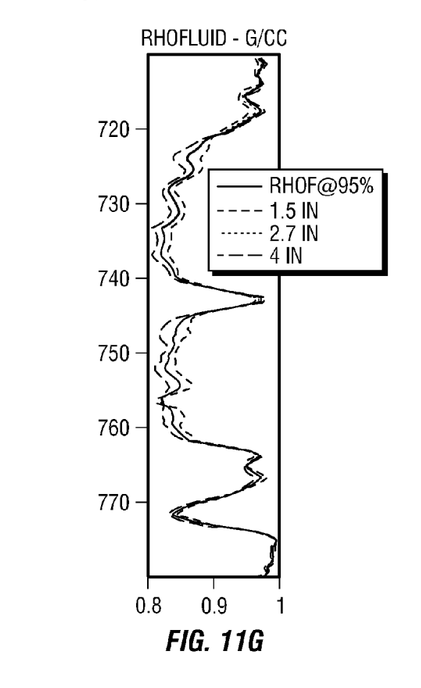
Figure 12A:
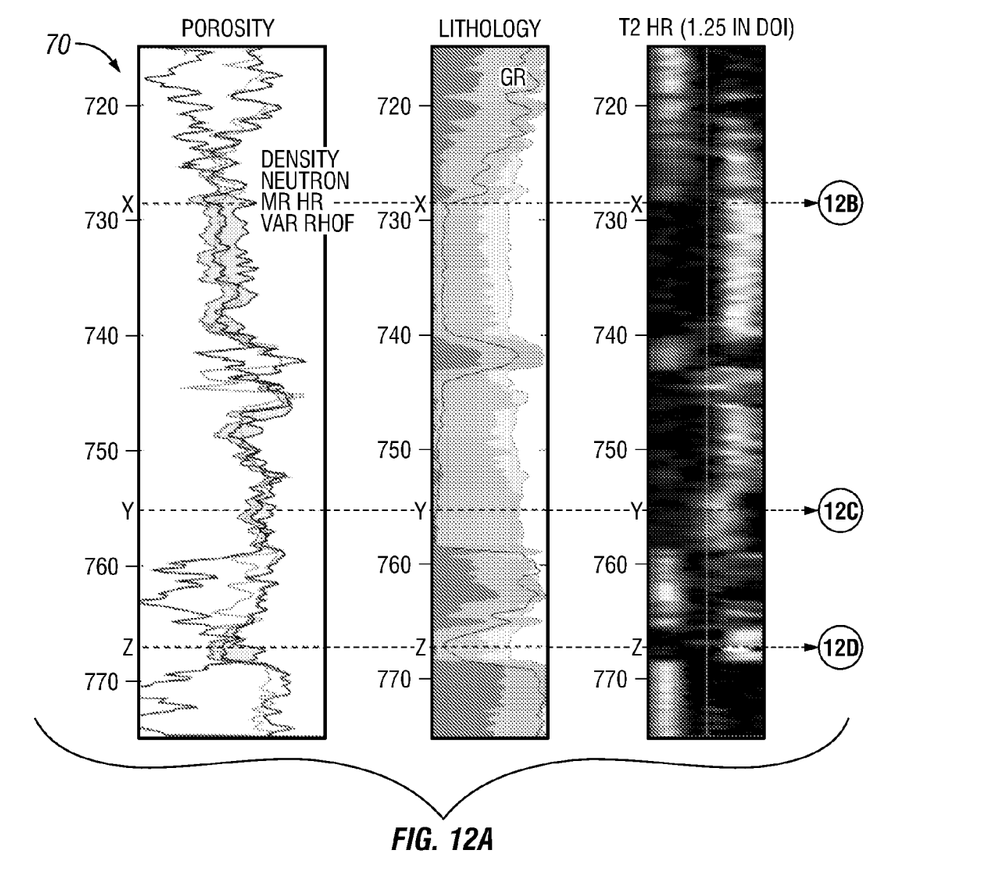
FIG. 12 is a graphical representation of a porosity comparison, according to an embodiment of the present invention.
Figure 12B:
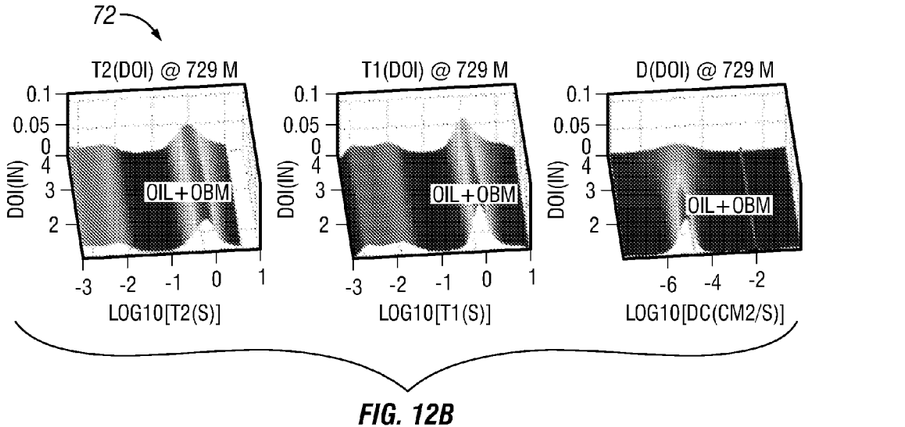
Figure 12C:
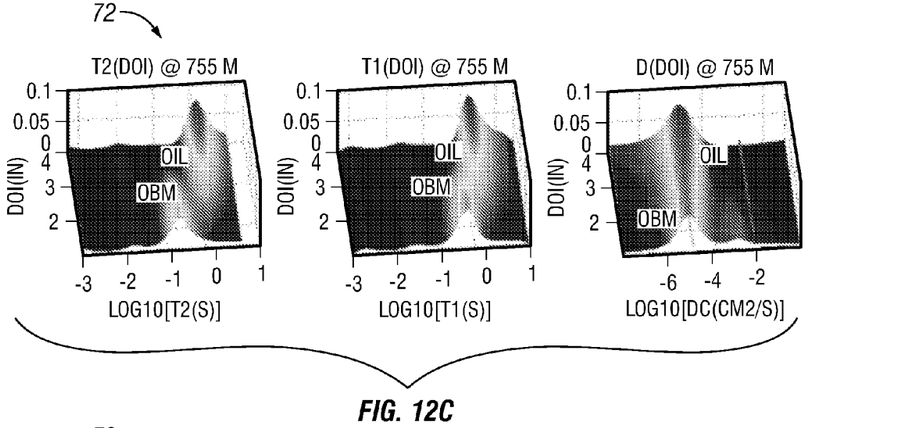
Figure 12D:
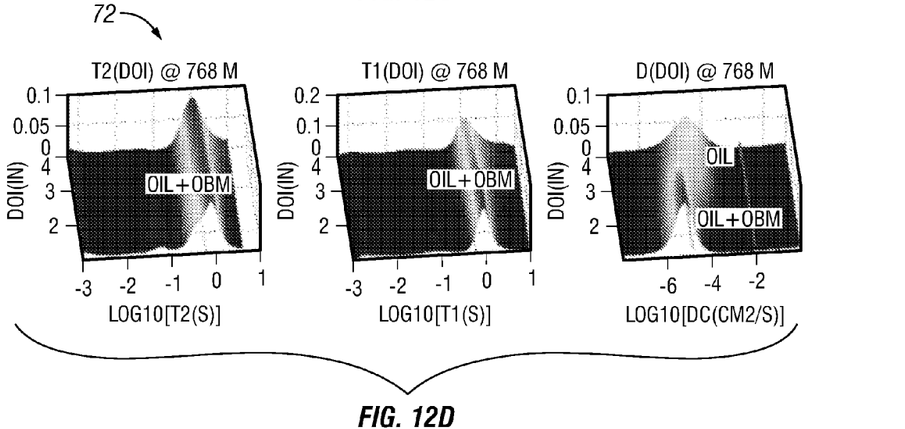

Using the parameters listed above, total porosity can be computed via processor based system 28 with the DMR technique that is well established in the art and combines density and high-resolution NMR logs correcting the effect of density and hydrogen index. In FIG. 8, a first track of a plurality of tracks 62 illustrates total/density porosity. With further reference to FIG. 8, radial fluids distribution D-T1 maps 64 also are provided for the gas zone, oil zone and water zone, respectively. Density porosity also is computed with the variable fluid density. The agreement between these results and DMR results is excellent as shown in the crossplot of FIG. 9. The intervals where the two porosities disagree are where the fluids change significantly radially.

Referring again to FIG. 8, within the gas zone, the D-T1 maps show significant OBM invasion at 1.5 in DOI that disappears at 2.7 in DOI. Within the oil zone, the D-T1 maps show only OBM at 1.5 in DOI and a mix of OBM and native oil at 2.7 in DOI. Finally, within the water zone, the D-T1 maps show increasing water content with increasing DOI.

Example 2

Oil-Bearing Reservoirs

A second example is provided on oil-bearing sandstone reservoirs drilled with OBM. In this example, the sands have variations in grain size and shaliness that control permeability and therefore the OBM invasion. They also have excellent porosity and permeability.

Referring to FIG. 10, openhole logs 66 are illustrated and include a high-resolution 1D NMR T2 log in track 4. The oil intervals are between the density and neutron logs illustrated in track 2. The separation between the density and neutron logs appears to correlate with the free fluid volume seen on the T2 distribution. In general, free fluid with long T2 corresponds to an anticorrelation of the density-neutron logs. However, in this example at the interval around 750 m-760 m, free fluid with short T2 corresponds to a correlation of the density-neutron logs.

According to one embodiment, the well may be logged in a single pass with a saturation-profiling mode (3D NMR) for fluid evaluation at, for example, 1.5 in DOI, 2.7 in DOI and 4 in. DOI. The fluid data can be processed on processor based system 28 according to a four dimensional (4D) NMR technique. In this example, fluid parameters are the same as those described above. The processed data results can be displayed on, for example, output 36, as illustrated in FIG. 11.

In FIG. 11, a plurality of tracks 68 is illustrated. The first 3 tracks display T2, T1 and D respectively for the 1.5 in DOI dataset. The fluid volumes for all 3 DOIs are displayed in track 4, track 5, and track 6, respectively. Track 7 shows the variable fluid densities at all DOIs and the estimated fluid density at 95% response (labeled as rhof). It can be seen that the fluid density in the sands averages 0.83 g/cc. In particular, the NMR fluid density at 2.7 in DOI is a good approximation to the effective fluid mixture density that the density log would provide, as predicted by equation (4).

At the top reservoir at 729 m, for example, a large density-neutron separation is shown at point X of FIG. 12 but with an anticorrelation (mirror curves). In the middle reservoir, a point Y at 755 m also shows density-neutron separation but with a correlation (parallel curves). In a bottom reservoir, a point Z at 768 m shows density-neutron separation with an anticorrelation (mirror curves).

Referring again to FIG. 12, the T2, T1 and D distributions (see track 70) versus DOI maps (see map 72) are extracted at the above depths to understand the fluids distribution effects on the nuclear logs. The information can be displayed on output 36. In this example, a porosity comparison is made between NMR and the variable fluid density techniques in the first track (see FIG. 12). The radial T2, T1, D maps 72 are illustrated for the top, middle and bottom reservoirs, respectively.

At point X and point Z, the maps show a consistent "single" fluid at all DOIs that is interpreted as formation oil with little OBM filtrate invasion. In this case, both density and neutron logs are affected by the hydrocarbon effect.

At point Y, the maps clearly show a fluid change with increasing DOI. The fluid close to the wellbore is essentially OBM filtrate. In this example, the radial depth of change occurs at about 3 in. in the formation where native oil is seen increasing with deeper DOI. This explains the short T2 seen at 755 m on the high-resolution T2 log (1.25 in DOI) displayed in track 3. In this case, the neutron log indicates different fluid than the density log, leading to the correlation between the two logs. In other words, the neutron log is much more affected by the hydrocarbon effect than the density log. Thus, applying standard hydrocarbon-correction to both logs will result in pessimistic total porosity.

Figure 13:
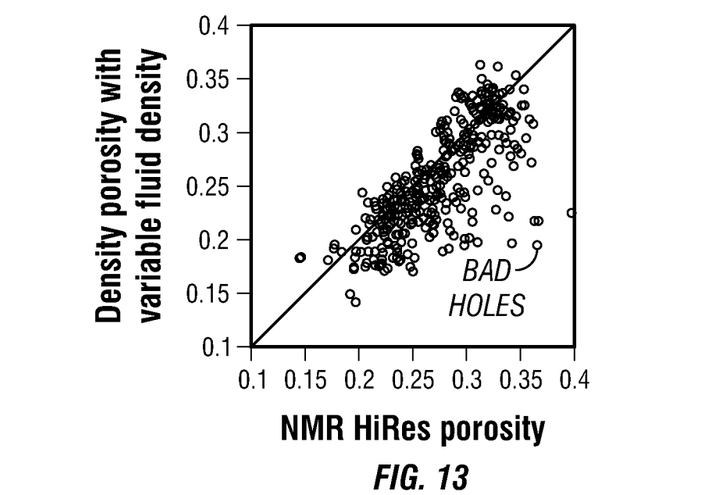
FIG. 13 is a graph illustrating a porosity comparison along x and y axes, according to an embodiment of the present invention.

Using a matrix density of 2.65 g/cc, determined from core data in nearby wells for example, density porosity can be computed using the variable fluid density determined via processor system 28 based on data acquired from NMR tool 22. The agreement with NMR high-resolution porosity is excellent as shown in the crossplot of FIG. 13. The disagreement at very high NMR porosities is caused by bad holes affecting the shallower high-resolution NMR log at 1.25 in. DOI.

Reconciliation of Density Porosity and NMR Porosity

In track 1 of FIG. 12, a consistent undercall of NMR porosity compared to density porosity is indicated. This is frequently the source of suspecting the NMR data validity since density porosity is often viewed as reference. The density porosity shown is computed with a default fluid density of 1 g/cc. A fluid density of 0.9 g/cc reduces the porosity undercall. The variable fluid density indicated in FIG. 11 demonstrates that an average fluid density value of 0.83 gcc will erase the porosity undercall.

For a 30 pu porosity formation, one can argue that an error on the matrix density is larger by at least a factor of two compared with an error on the fluid density. In practice, the opposite is true. Once the matrix density is known from core analysis, it is reasonable to assume that the same sands in the field have the same matrix density. However, one can never be sure of the status of the fluids invasion even if the same mud was used to drill other wells. There are simply too many parameters involved in the invasion process that cause the near-wellbore fluids distribution to change in the same sands from well to well.

Accordingly the system and methodology described herein can be used to improve the estimation of a fluid characteristic or characteristics in a well application. For example, the system can be used to acquire 4D NMR data at multiple depths of investigation. The acquired data can be processed on processor based system 28 to determine variable fluid mixture densities at multiple depths of investigation. For instance, system 28 can be used to process data with a 4D NMR joint-inversion of all data. Additionally, the processor based system 28 can be used to perform fluids volumetrics in T2, T1, and D for all depths of investigation. The system can further be used to verify the computed variable fluid mixture densities as compatible with a density log. The actual configuration of NMR tool 22 and processing system 28 may vary from one application to another. Similarly, the fluid density/porosity information displayed and the algorithms employed to calculate and/or display the information can vary from one application to another.

Figure 14:
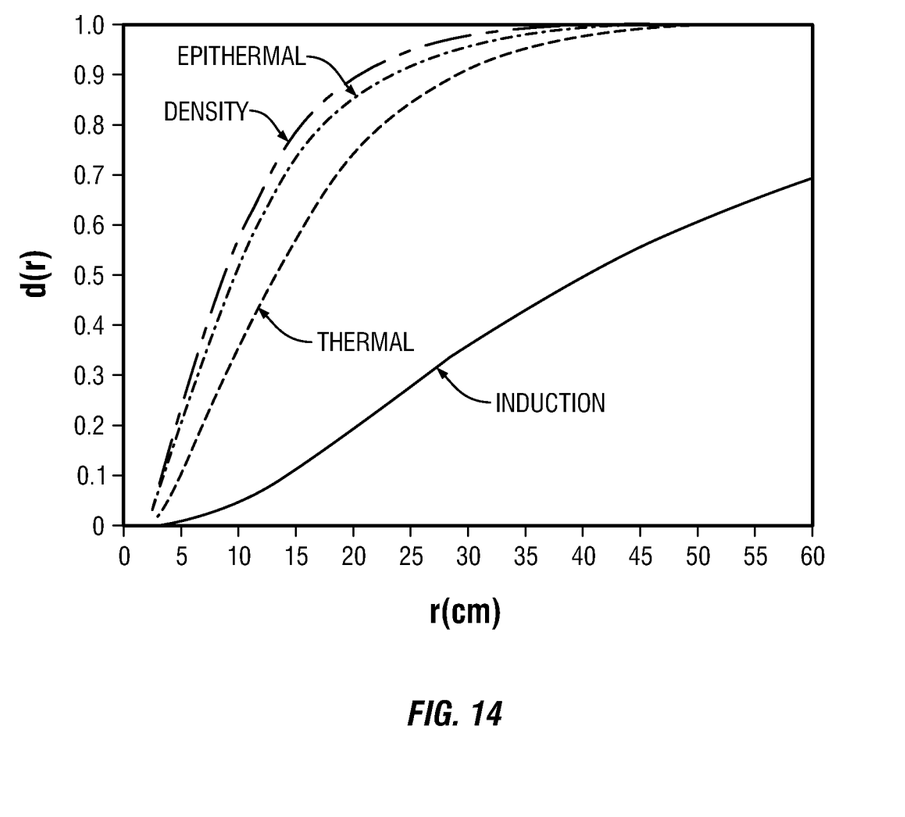
FIG. 14 is a graph of the radial response functions of induction logging tool, density logging tool, and neutron (thermal and epithermal) tool.

Application of this invention is not limited to density logs. A logging tool with approximately the same volume of investigation as the NMR tool may be used to practice this invention. One needs to know the radial response function of the tool and be able to derive the property of interest as a function of radial distance from the NMR results. Examples are neutron (thermal and epithermal) logging tool, induction logging tool, and dielectric permittivity logging tool individually or in combination. The radial response functions of the neutron and induction tools are shown in FIG. 14; the radial response function of dielectric logging tool is expected to be similar to the induction tool. Note that the response functions are dependent on the specific tool design and for induction tools for example, the transmitter to receiver distance can be adjusted to obtain a response functions with the proper range. The property of interest in neutron, induction, and dielectric permittivity logs is the fluid saturation from NMR and fluid conductivity that can be determined independently.

Accordingly, although only a few embodiments of the present invention have been described in detail above, those of ordinary skill in the art will readily appreciate that many modifications are possible without materially departing from the teachings of this invention. Such modifications are intended to be included within the scope of this invention as defined in the claims.

What is claimed is:

1. A method to determine a formation characteristic, comprising:
    using a nuclear magnetic resonance logging tool to acquire a first log data wherein the first log comprises a nuclear magnetic resonance log at a plurality of depths of investigation;
    using another logging tool to acquire a second log data;
    using a processor to:
    process the acquired first log data to determine a formation property at the plurality of depths of investigation;
    combine the formation property with a response of the second log to obtain an effective formation property; and
    produce and display a log of the formation characteristic using the effective formation property.

2. The method as recited in claim 1, further comprising using the processor to perform fluid volumetrics in D, T1, and T2 distributions for the plurality of depths of investigation.

3. The method as recited in claim 1, wherein the formation characteristic comprises density, porosity, resistivity, fluid saturation, and dielectric permittivity.

4. The method as recited in claim 1, wherein using the processor to process the acquired first log data comprises generating four dimensional nuclear magnetic resonance maps.

5. The method as recited in claim 1, wherein the combining comprises integrating, and or extrapolating.

6. The method as recited in claim 1, wherein the second log comprises at least one of a neutron log, a porosity log, an induction resistivity log, or a dielectric log.

7. The method as recited in claim 1, wherein the acquiring the first and the second log comprises acquiring data in a well drilled in a gas bearing formation.

8. The method as recited in claim 1, wherein acquiring the first and the second log comprises acquiring data in a well drilled in an oil bearing formation.

9. The method as recited in claim 1, wherein the acquiring the first and the second log comprises acquiring data by logging a well in a single pass.

10. The method as recited in claim 1, wherein the formation property comprises at least one of fluid saturation, fluid viscosity, fluid diffusion constant distribution, T1 distribution, T2 distribution, porosity, or permeability.

11. The method as recited in claim 1, wherein the response of the second log is a radial response.

12. A method to determine formation porosity of a region in a well of interest, comprising:
    using nuclear magnetic resonance logging tool to acquire a nuclear magnetic resonance log data at a plurality of depths of investigation;
    processing, using a processor, the acquired nuclear magnetic resonance log data to determine a variable fluid saturation at the plurality of depths of investigation;
    obtaining a density log data using a density logging tool;
    combining, using the processor, the variable fluid saturation with fluid density and a radial response of the density log to obtain an effective fluid density; and
    producing and displaying, using the processor, a log of the formation porosity based on a determined matrix density of the region of the well of interest and the effective fluid density.

13. The method as recited in claim 12, wherein acquiring the nuclear magnetic resonance log data comprises using a radial fluid profiling.

14. The method as recited in claim 12, wherein the processing of the acquired nuclear magnetic resonance log data comprises a four dimensional nuclear magnetic resonance technique.

15. The method as recited in claim 12, wherein the combining comprises at least one of integrating or extrapolating.

16. The method as recited in claim 12, wherein the acquiring and the obtaining comprise acquiring and obtaining data in the well of interest, the well of interest being drilled with oil-base mud.

17. The method as recited in claim 12, wherein the well of interest is drilled in a gas bearing or an oil bearing formation.

18. The method of claim 12, wherein the matrix density of the region of the well of interest is determined via core analysis of other wells in proximity to the well of interest or by spectroscopy logging.

19. The method of claim 18, wherein the core analysis is performed prior to using the nuclear magnetic resonance logging tool to acquire the nuclear magnetic resonance log data.

20. A system to determine a formation characteristic, comprising:
    a nuclear magnetic resonance tool capable of measuring a formation response at a plurality of depths of investigation;
    a second logging tool; and
    a processor to determine a formation property at the plurality of depths of investigation, combine the formation property with a radial response of a log acquired using the second logging tool, and determine the formation characteristic.

21. The system as recited in claim 20, wherein the formation characteristic comprises at least one of density, porosity, resistivity, fluid saturation, or dielectric permittivity.

22. The system as recited in claim 20, wherein the second logging tool comprises at least one of a neutron logging tool, a porosity logging tool, an induction resistivity logging tool, or a dielectric logging tool.

23. The system as recited in claim 20, wherein the formation property comprises at least one of fluid saturation, fluid viscosity, fluid diffusion constant, T1 distribution, T2 distribution, porosity, or permeability.

* * * * *